(12) United States Patent
Boyle et al.

(10) Patent No.: US 6,837,898 B2
(45) Date of Patent: Jan. 4, 2005

(54) INTRALUMINAL DELIVERY SYSTEM FOR AN ATTACHABLE TREATMENT DEVICE

(75) Inventors: William J. Boyle, Fallbrook, CA (US); Benjamin Huter, Murrieta, CA (US); John E. Papp, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 315 days.

(21) Appl. No.: 10/000,832

(22) Filed: Nov. 30, 2001

(65) Prior Publication Data
US 2003/0105484 A1 Jun. 5, 2003

(51) Int. Cl.[7] .............................................. A61M 29/00
(52) U.S. Cl. ...................................................... 606/200
(58) Field of Search ................................ 606/200, 114, 606/113, 127; 600/434, 585

(56) References Cited

U.S. PATENT DOCUMENTS

| 5,634,942 | A | 6/1997 | Chevillon et al. |
| 5,645,589 | A | 7/1997 | Li |
| 5,893,869 | A | 4/1999 | Barnhart et al. |
| 5,910,154 | A | 6/1999 | Tsugita et al. |
| 5,911,734 | A | 6/1999 | Tsugita et al. |
| 5,928,258 | A | 7/1999 | Kahn et al. |
| 5,941,896 | A | 8/1999 | Kerr |
| 5,976,172 | A | 11/1999 | Homsma et al. |
| 6,027,520 | A | 2/2000 | Tsugita et al. |
| 6,051,015 | A | 4/2000 | Maahs |
| 6,152,946 | A | 11/2000 | Broome et al. |
| 6,171,327 | B1 | 1/2001 | Daniel et al. |
| 6,179,859 | B1 | 1/2001 | Bates et al. |
| 6,203,561 | B1 | 3/2001 | Ramee et al. |
| 6,214,025 | B1 | 4/2001 | Thistle et al. |
| 6,277,138 | B1 | 8/2001 | Levinson et al. |
| 6,325,815 | B1 | 12/2001 | Kusleika et al. |
| 6,328,755 | B1 | 12/2001 | Marshall |
| 6,336,934 | B1 | 1/2002 | Gilson et al. |
| 6,344,049 | B1 | 2/2002 | Levinson et al. |
| 6,355,051 | B1 | 3/2002 | Sisskind et al. |
| 6,361,546 | B1 | 3/2002 | Khosravi |
| 6,485,501 | B1 * | 11/2002 | Green .......................... 606/200 |

FOREIGN PATENT DOCUMENTS

WO      WO 02/32496      4/2002

OTHER PUBLICATIONS

U.S. Publication No.: 2002/012472 A1; Joseph Garner, et al., Intravascular Filter Retrieval Device Having an Actuatable Dilator Tip, Publication Date Sep. 5, 2002.

* cited by examiner

Primary Examiner—Kevin T. Truong
(74) Attorney, Agent, or Firm—Fulwider Patton Lee & Utecht LLP

(57) ABSTRACT

A system for delivery of an intraluminal treatment device is provided. A guide wire having a recessed portion is combined with an intraluminal treatment device having a mechanism for securing the intraluminal treatment device to the recessed portion. This system permits an intraluminal treatment device to be secured to the guide way prior to or after the intraluminal delivery of the guide wire.

18 Claims, 6 Drawing Sheets

INTRALUMINAL DELIVERY SYSTEM FOR AN ATTACHABLE TREATMENT DEVICE

BACKGROUND OF THE INVENTION

The present invention relates to intraluminal medical devices for the treatment of vascular diseases. More particularly, this invention relates to a system which allows an intraluminal treatment device or other devices to be secured onto a guide wire either during or pretreatment. An example of such an intraluminal device includes an embolic cage configured to prevent emboli from being released into the bloodstream.

Atherosclerosis and other vascular occlusive diseases are becoming prevalent today in many developed countries. In such diseases, the flow areas of blood vessels become narrowed or occluded by the buildup of plaque on the walls of the vessels, leading to ischemia, and depending upon the location of the vessel, damage to the organ or limb. A number of surgical and percutaneous procedures have been developed for treating stenosis in the coronary arteries and carotid arteries.

Embolic cages are known in which filter elements are deployed against the walls of a vessel distal to a stenosis. Such filters typically comprise a polymer or wire sac mounted on a distal region of a guide wire or angioplasty catheter, and permit blood flow through the filter while trapping emboli. Once treatment of the stenosis is completed, the filter containing the captured emboli is contracted and withdrawn from the vessel. Embolic cages may also be considered "treatment devices" in a broad sense of the term.

The purpose of intraluminal procedures is to allow blood to flow without obstruction. Such procedures usually involve the percutaneous introduction of an intraluminal treatment device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A catheter is usually used to capture the shaved plaque or thrombus from the bloodstream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, pieces of plaque material are sometimes generated during an intraluminal procedure and become released into the bloodstream.

When any of the above-described procedures are performed in the carotid arteries, the release of emboli into the circulatory system should be avoided. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, there can be complications associated with such systems if the vacuum catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

Embolic cages and other intraluminal treatment devices have been known to be fixedly attached to a guide wire. Guide wires are highly flexible wire elements which are advanced through the vascular system and across cites of vascular occlusive disease. The normal anatomy of the vascular system may be highly tortuous creating challenges to access by guide wires. Vascular occlusive diseases may severely narrow and even totally occlude the normal anatomy of the vascular system. Furthermore, the presence of calcified (hardened) plaque may present additional difficulties in accessing and crossing the site of vascular occlusive disease.

To meet these difficulties in vascular access, guide wires are often very narrow in gauge and highly flexible. To perform the required vascular treatment, intraluminal treatment devices are generally larger in diameter than guide wires and somewhat less flexible. Therefore, what is needed in the art is a system for delivering a highly flexible guide wire with an attached intraluminal treatment device. The present invention meets this need.

SUMMARY OF THE INVENTION

The present invention includes an intraluminal treatment device (such as an embolic cage) slidably engaged over a guide wire. The guide wire may be configured to fixedly secure the intraluminal treatment device once it has been advanced to a region near the distal tip of the guide wire. The intraluminal treatment device may also be configured to grasp the guide wire at this location. Once secured, the intraluminal treatment device may be advanced or retracted with the guide wire. Alternatively, the intraluminal treatment device may be fixedly secured to the guide wire prior to initiating the intraluminal procedure. This alternative permits versatility of the system, possibly for use with diseased vessels which are determined to be easily crossed with the treatment device secured to the guide wire.

Those of skill in the art of intraluminal procedures often use terms of art to refer to the orientation of medical devices and the body passageways. For instance, the term "proximal" may refer to the direction towards the operator of the medical device. The term "distal" may refer to the direction away from the operator. Thus, an intraluminal device may be advanced distally and withdrawn proximally.

The guide wire is preferably configured with a recessed portion along its length. This recess may be formed in the guide wire either by a localized narrowing of the diameter of the guide wire or by placing larger gauge bushings on the guide wire to form a recess therebetween. The recess may have various configurations based on the method of forming the recess and the desired method of capturing the intraluminal device.

The intraluminal device may be configured with appendages in the form of spring-loaded detents which grasp the recessed region of the guide wire. These appendages may be formed from small flexible beams biased to press against the guide wire. When these beams reach the recessed portion of the guide wires the spring forces of the flexible beams resist sliding out of that portion. The detent may also be formed of a grommet with an inwardly bent end.

An example of a procedure utilizing the present invention may proceed as follows: Once the vascular system has been accessed, a guide wire having a recessed portion may be advanced toward a site of vascular occlusive disease. The distal tip of the guide wire crosses the site and is advanced until the recessed portion of the guide wire also crosses the site. A catheter housing a collapsed embolic cage is advanced over the guide wire until it also crosses the site of the vascular occlusive disease. The embolic cage equipped with spring-loaded appendages is then advanced over the guide wire until the appendages extend into the recessed portion of the guide wire. At this point the embolic cage is now captured by the guide wire and may be advanced or retracted along with the guide wire. The embolic cage may be expanded prior to or after being captured by the guide wire. Once the embolic cage is expanded and captured the delivery catheter may be withdrawn.

During intraluminal treatment of the vascular occlusive disease, the embolic cage remains expanded to capture any emboli that may be released during treatment. Once treatment is complete, the embolic cage may be collapsed and removed along with the guide wire.

DETAILED DESCRIPTION OF THE PREFERRED EMBODIMENTS

The present invention relates to treatment devices for vascular disease. The invention permits a treatment device such as an embolic protection cage to be securely affixed to a guide wire either during or just prior to the intraluminal procedure. In general terms, the treatment device may be advanced over the guide wire until it reaches a recess in the guide wire at which point the treatment device grasps the guide wire.

A delivery system 20 conforming to the present invention may include a guide wire 22 having a recessed portion 24, and an embolic cage 26 having at least one detent 28. The embolic cage is preferably mounted onto the guide wire in such a configuration that the embolic cage freely slides over the guide wire. Once the detents on the embolic cage engage the recessed portion of the guide wire, however, the embolic cage is securely affixed and will advance and retract with the guide wire.

Because of the environment that guide wires are used, and the purpose they serve, it is desirable to have several basic features for most, if not all, guide wires. The guide wire must be able to navigate and advance within the lumens of a patient, and come into contact with delicate tissue. For this reason, the guide wire usually requires a soft, flexible tip coil 23 which can be manipulated without causing injury to the vessel walls. It also must be sufficiently maneuverable to reach the required destination, which requires stable torsional characteristics, and a rigid proximal shaft that can be pushed to advance the guide wire. This is particularly true when a medical device is attached near the distal end of the guide wire. Often, these characteristics are difficult to achieve, since one feature tends to negate the other. It is also desirable for the outer diameter of the guide wire to fit properly within the inside diameter of the lumen within which it is disposed.

Conventional guide wires for use in angioplasty, stent delivery, atherectomy and other vascular procedures generally comprise an elongated core member with one or more tapered section near the distal end and a flexible body member such as a helical coil disposed about distal portion of the core member. A shapable member, which may be the distal end of the core member or a separate shapable ribbon which is secured to the distal end of the core member enables the physician to shape or curve the tip as needed for maneuvering purposes. Torquing means are provided on the proximal end of the core member to rotate, and thereby steer, the guide wire while it is being advanced through the patient's vasculature. The tip of the guide wire should be highly flexible and atraumatic so as not to damage or perforate the vessel while the portion behind the tip should be increasingly stiff to better support the medical device attached to the guide wire.

Figure 1:
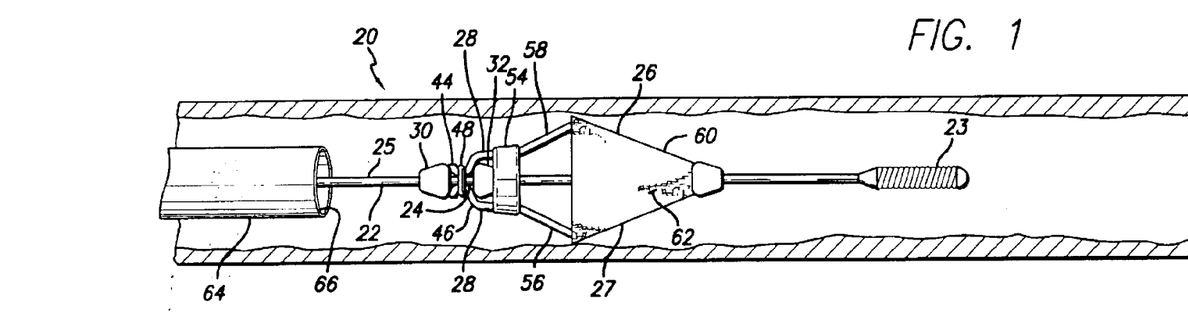
FIG. 1 is a side view of an intraluminal treatment device.
Figure 2:
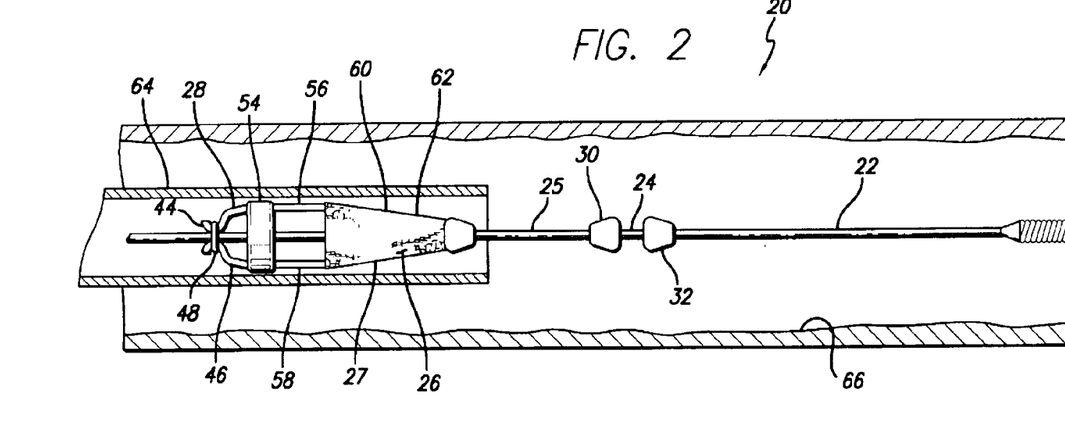
FIG. 2 is a side view of an intraluminal treatment device.
Figure 3:
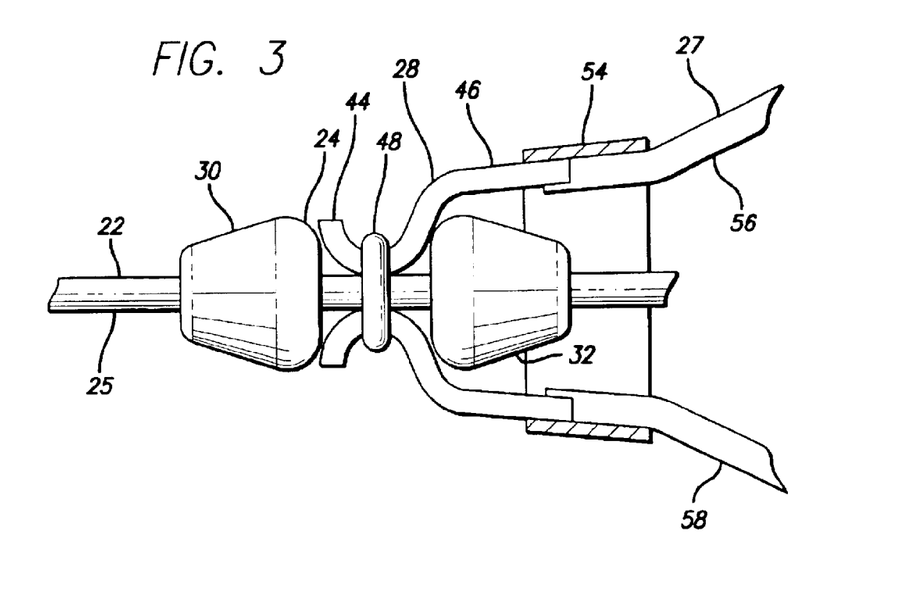
FIG. 3 is an enlarged side view of a portion of an intraluminal treatment device.

The recessed portion 24 on the guide wire 22 of the present invention may be formed in one of several configurations. As depicted in FIGS. 1–3 the recessed portion may be formed between a proximal bushing 30 and a distal bushing 32. These bushings are adhered to the guide wire by conventional means such as gluing, spot welding, or soldering. These bushings may be formed of any hard plastic or metal. Preferably, the bushings are formed from a radiopaque material allowing their location within the vascular system to be determined by fluoroscopy. Alternatively, bushings 30 and 32 may be part of a combined bushing 33 with a recess in the center.

As depicted in FIG. 2, the proximal bushing 30 and distal bushing 32 may both be located in a region of constant diameter on the guide wire 22. This is considered the nominal diameter 25 of the guide wire. Thus, in this configuration, the recessed region 24 is simply the area between the bushings and does not necessarily have a diameter different from that of the surrounding guide wire.

Although the bushings 30, 32 may have any number of shapes, the proximal bushing 30 preferably tapers in the proximal direction and the distal bushing 32 preferably tapers in the distal direction. This tapering facilitates any forced translation of an object compressed onto the guide wire 22 into the recessed portion 24 of the guide wire and inhibiting any forced translation of an object compressed onto the guide wire out of the recessed portion of the guide wire. For example, an object compressed onto the guide wire and located proximal to the proximal bushing which is translated distally, will ride up the proximal taper of the proximal bushing until the object passes over the bushing into the recessed portion. Likewise, a similarly compressed object located distal to the distal bushing which is translated proximally, will ride up the distal taper of the distal bushing until the object passes over the bushing into the recessed portion. However, an object compressed onto the guide wire and located within the recessed portion will receive greater resistance in translating proximally or distally because both bushings are tapered away from the recessed portion.

Figure 4:
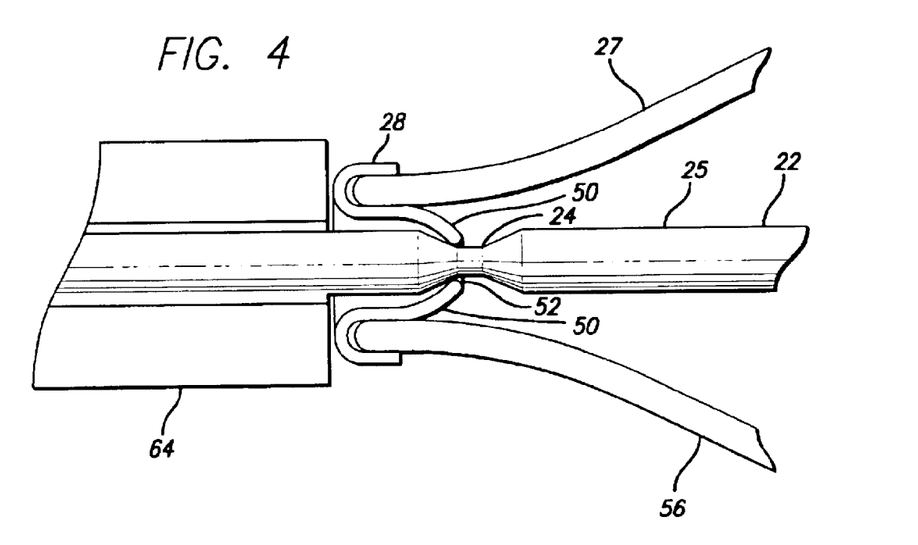
FIG. 4 is an enlarged side view of a portion of an intraluminal treatment device.

As depicted in FIGS. 4 and 5, the recessed portion 24 of the guide wire 22 may also be formed by a localized narrowing of the diameter of the guide wire. This narrowing may be formed during the initial manufacturing process of the guide wire, such as by the use of centerless grinders to grind down the nominal diameter 25 of the guide wire.

Figure 5A:
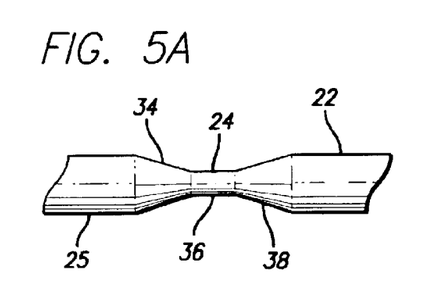
FIGS. 5A–5E are side views of a portion of a guide wire having recessed areas.
Figure 5B:
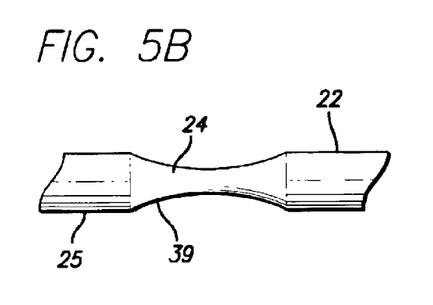
Figure 5C:
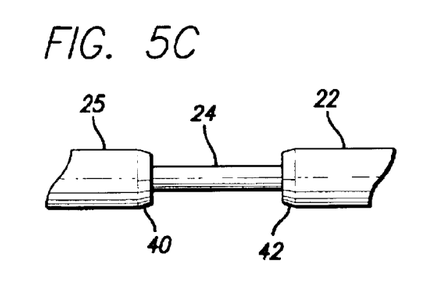

As depicted in FIGS. 5A–5E, the recessed portion 24 of the guide wire 22 may have a variety of shapes. One shape has a proximal taper 34, a flattened portion 36, and a distal taper 38. In this particular configuration, the detents 28, while securely compressed against the guide wire 22, may smoothly transition from the nominal diameter of the guide wire into the recessed portion. Once inside the recessed portion, particularly while within the flattened portion 36, the compression of the detents resists the translation of the detents back to the guide wires nominal diameter 25. To maximize the smoothness of the recessed portion, the tapers and flattened portions may be combined into a single parabolic shaped recess 39 as depicted in FIG. 5B.

Another embodiment of the recessed portion 24 of the guide wire 22 includes an abrupt change in diameter, such as on a slot. As shown in FIG. 5B, the configurations may include a proximal chamfer 40 and a distal chamfer 42 to prevent snagging the luminal walls and intraluminal devices. This configuration may maximize the resistance involved in removing the detent 28 from the recessed portion 24.

Figure 5D:
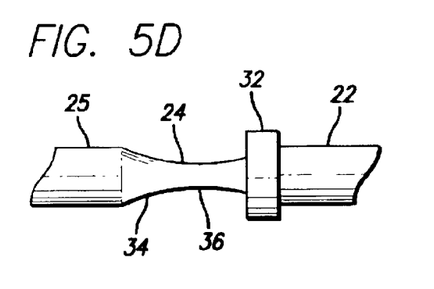

The configuration of the recessed portion 24 of the guide wire 22 may also include various components of the above-described configurations. Thus, the recessed portion may have a taper on one end and an abrupt diameter change on the other. Furthermore, as depicted in FIG. 5D, the recessed portion may include a combination of tapers and bushings.

Figure 5E:
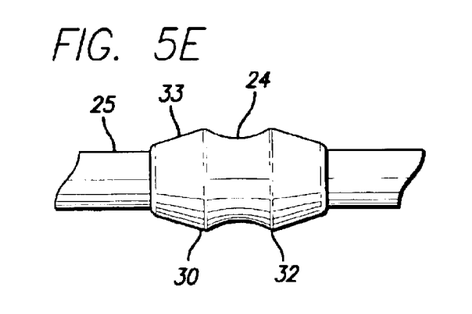

In another embodiment, as depicted in FIG. 5E, the recessed portion 24 may be formed entirely within a combined bushing 33. The combined bushing thereby includes a proximal bushing 30, a distal bushing 32 and a recessed portion formed therebetween. This combined bushing may be formed similarly to conventional bushings.

The intraluminal treatment device 27 of the present invention typically includes at least one detent 28. In the figures, the treatment device is depicted as an embolic cage 26 with multiple detents. The exact number and configuration of these detents may vary with the size and application of the treatment device.

The detents may be formed of metal or hard plastics but are preferably formed of a material which is highly springy or elastic. This permits the detents to be compressed onto the outer diameter of the guide wire both at its nominal diameter 25 and at the recessed portion 24. The detents may also be composed of a radiopaque material for detection of their position through fluoroscopy.

In a particular embodiment, as depicted in FIG. 3, the detents 28 may be shaped with a U-shaped end 44, and a body extension 46. This U-shaped end is compressed against the guide wire 22 by biasing the body extension radially into the guide wire. Thus, in configurations with multiple detents, the plurality of U-shaped ends are each distributed around the guide wire with the body extensions extending generally outwardly. The U-shaped ends may include relatively sharp ends, which might be more accurately described as V-shaped.

The U-shaped ends 44 of the detents 28 compress against and freely slide over the nominal diameter 25 of the guide wire 22. The U-shaped ends may also be translated into the recessed portion 24 of the guide wire. As described above, this may be accomplished either by forcing the detent over the proximal bushing 30 in configurations having bushings, or sliding the detent down the proximal taper 34 of configurations having tapers. Although prior to being captured by the recessed portion, the treatment device 27 and detents are typically located proximal to the recessed portion, it is conceived that the detents may enter the recessed portion from distal to the recessed portion. Thus, the detents may also be forced over the distal bushing 32 or slid down the distal taper 38 to enter the recessed portion. Once the U-shaped ends of the detents enter the recessed portion of the guide wire the compresses forces imparted by the body extension 46 of each detent resist the expansion necessary to force the detent out of the recessed portion.

While captured in the recessed portion 24 of the guide wire 22, the treatment device 27 no longer freely slides over the guide wire. Thus, the treatment device translates proximally and distally in concert with the guide wire. At the same time, the guide wire may be freely rotated without changing the orientation of the treatment device.

Although the sizing of the detents 28 and bushings 32, 34 is variable, it is important to ensure that the outer diameter of each bushing is sufficiently large enough to require a significant force to translate the detents out of the recessed portion 24 of the guide wire 22. The nominal diameter 25 of guide wires for coronary and carotid uses are typically in the range of 0.010" and 0.018" in diameter. The proximal and distal bushings forming the recessed portion may be on the order of twice the dimension of the nominal diameter. In a particular embodiment of the present invention, the diameter of the flexible tip coil 23 is sized larger than the distal bushing 32. This is an added safety precaution in the unlikely event the detents 28 of the treatment device 27 are forced distal to the distal bushing. In this event the treatment device will remain on the guide wire as it will be prevented from passing over the flexible tip coil.

As depicted in FIG. 3, a particular embodiment of the present invention may include a compressive strap 48 around the detent 28. This is particularly useful when multiple detents are used having U-shaped ends 44. The compressive strap adds to the compressive force associated with biasing the detent into the guide wire. The compressive strap is preferably composed of highly elastic material.

In another embodiment, as depicted in FIG. 4, the detent may be formed from a grommet 50 with an inwardly bent end 52. The grommet may be generally cylindrical in shape and positioned to freely slide over the guide wire 22. The inwardly bent end is configured to compress against both the nominal diameter 25 of the guide wire and the recessed portion 24 of the guide wire. In this manner, the inwardly bent end of the grommet resists translation while in the recessed portion of the guide wire by resisting the expansion required to translate beyond the recessed portion.

The other end of the grommet 50 may fold outwardly back over itself. This permits attachment between the grommet and the treatment device 27. The grommet may be adhered to the treatment device using conventional means, such as by gluing, welding, press-fitting or stitching.

Likewise, an embolic cage 26 may be attached to a detent 28 having a U-shaped end 44 and a body extension 46 with a sleeve 54 wrapped around both. Embolic cages include many variable designs and the present invention is configured to secure all such designs to the guide wire with minimal modifications. Embolic cages typically include expandable members 56 in conical arrangements. A first conical arrangement 58 expands distally and includes expandable members which may be attached to the sleeve. A second conical arrangement 60 tapers distally and includes expandable members as well as webbing 62 configured to catch emboli.

Embolic cages 25 are typically collapsible for delivery within a delivery catheter. Thus, the first conical arrangement 58 attaches to the second conical arrangement 60 in such a manner as to allow both to be collapsed. The expandable members 56 are typically composed of highly elastic metal, such as a Nickel Titanium alloy (NiTi), which permits for collapsing and expansion of the embolic cage. Likewise both the webbing 62 and the sleeve 54 are typically composed of sufficiently pliable materials as to permit the same collapsing and expansion.

The sleeve 54, as depicted in FIG. 3, may wrap around both the expandable members 56 of the embolic cage 26 and the body extensions 46 of the detents 28. The expandable members and body extensions may be attached to the sleeve or directly attached to each other. Conventional means such as a gluing, welding or stitching may be used for these attachments.

The sleeve 54 may be composed of a fabric or a plastic sheet or other pliable material. The sleeve preferably may be compressed for delivery and retraction of the treatment device 27. Alternatively, the sleeve 54 may be formed of a rigid material such as steel and of such a diameter that allows it to fit inside the delivery catheter 64. The sleeve may also function to impart the inward bias of the body extensions 46 of the detent 28. By forming the sleeve in a conical shape with the body extensions extending inwardly from the small end of the cone, the body extensions will tend to be biased inwardly.

Regardless of the specific configuration of the detent 28, it is preferable that the detent is configured to allow the treatment device 27 to be collapsed for delivery, expanded for treatment and recollapsed for withdrawal. As depicted in FIG. 2, the treatment device is typically collapsed to fit within a delivery catheter 64. This catheter may encompass the entire device for delivery to the recessed portion 24 of the guide wire 22 once the guide wire is advanced to the desired location. The delivery catheter may be configured as a conventional delivery catheter, or preferably the delivery catheter may be configured with modifications conforming to the present invention.

Figure 6:
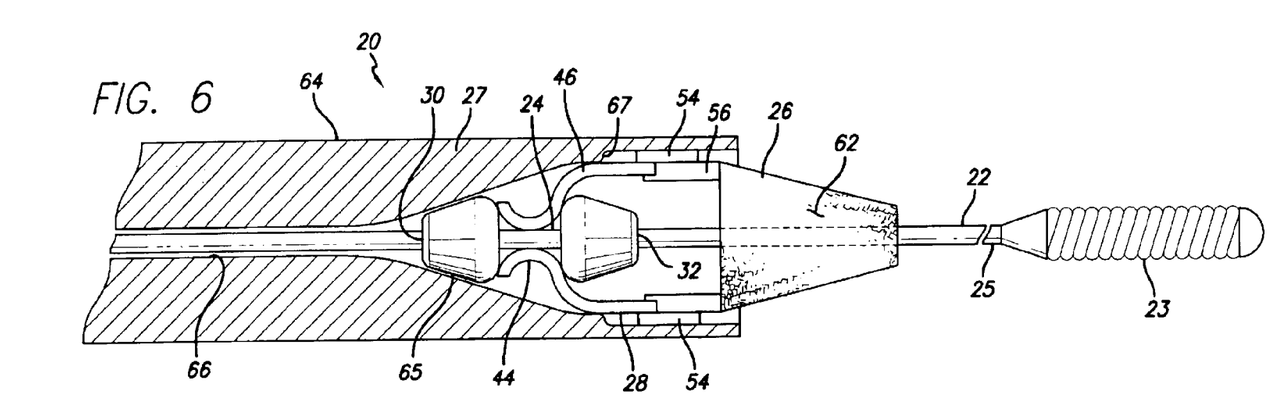
FIG. 6 is a side view of a delivery system for an intraluminal treatment device.

In another embodiment, as depicted in FIG. 6, the delivery catheter 64 includes a modified interior diameter 66. The interior diameter may be tightened to a smaller diameter proximal to the position of the treatment device 27. This smaller diameter may be accomplished by modifying the thickness of the wall of the catheter. Conventional methods of catheter manufacture provide the means for this modification. This smaller diameter may perform multiple roles in the use of this invention. First, the narrower diameter may be used to push the treatment device along the guide wire. To accomplish this the modified interior diameter may form a ridge 67. The ridge may be positioned and sized to push against the sleeve 54 of the treatment device. In this manner the treatment device may be translated along the guide wire 22 without impacting more delicate portions of the treatment device.

Second, the modified interior diameter 66 of the delivery catheter 64 may form an internal taper 65. The internal taper may be positioned and sized to impact upon the proximal bushing 30. This facilitates translating the treatment device 27 up to, but not past the recessed portion 24. Thus preventing the delivery catheter from pushing the detent 28 of the treatment device beyond the recessed portion 24.

Figure 7:
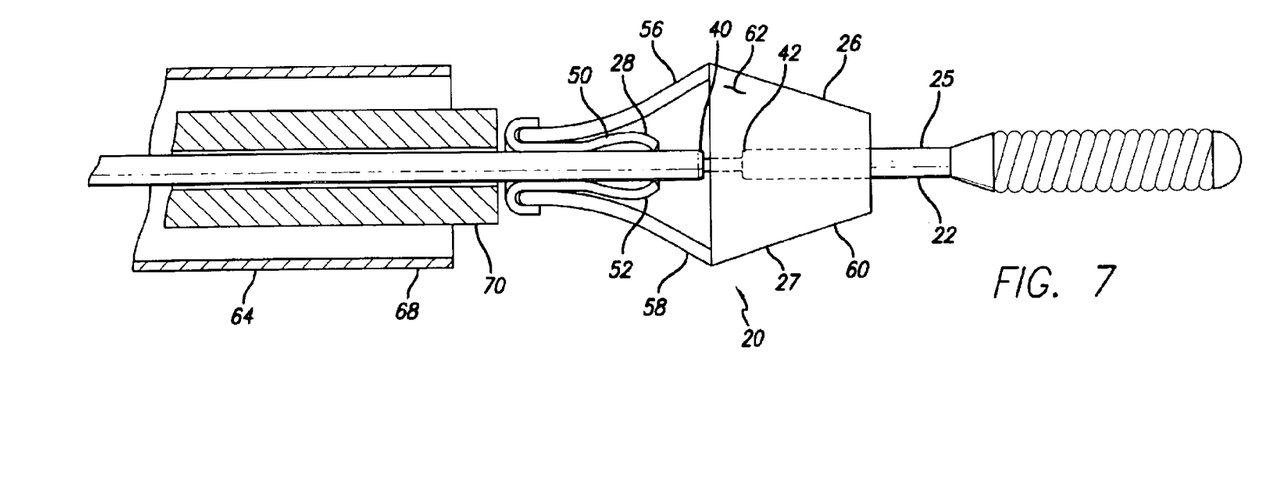
FIG. 7 is a side view of a delivery system for an intraluminal treatment device.

Another embodiment, as depicted in FIG. 7, includes a delivery catheter 64 with two components. The first, outer catheter 68, may encompass the treatment device 27. The second, inner catheter 70 is used to push the treatment device. The inner catheter may also be sized to prevent pushing the treatment device past the proximal bushing 30.

Figure 8:
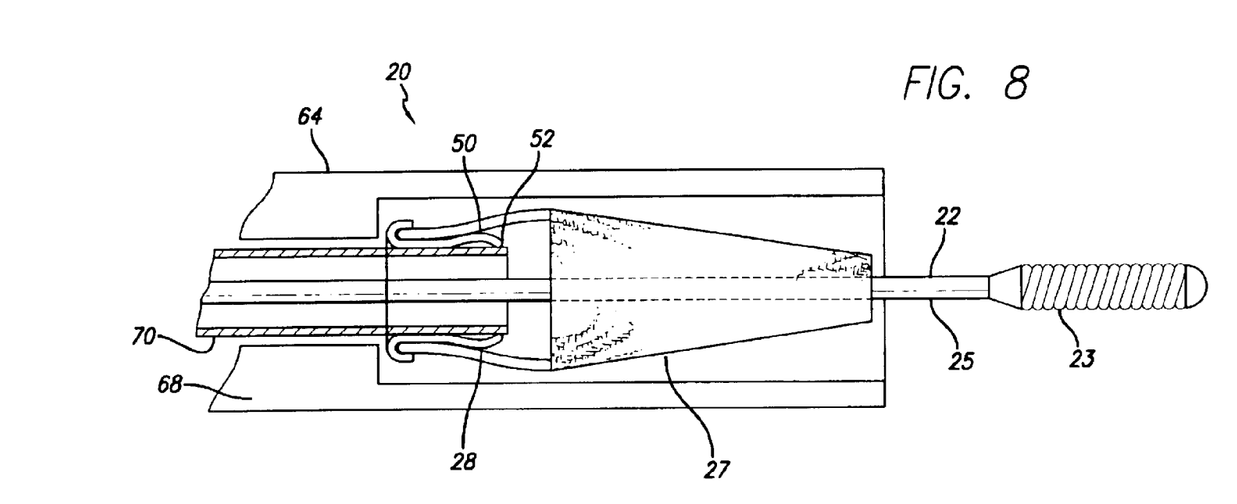
FIG. 8 is a side view of a delivery system for an intraluminal treatment device.

In another embodiment, as depicted in FIG. 8, the inner catheter 70 may be configured to prevent the detents 28 from impacting the guide wire 22 during delivery. This configuration may be used with both the U-shaped end 44 configuration of the detent, as well as the inwardly bent end 52 configuration of the detent. In this configuration, the inner catheter resides between the collapsed detent and the guide wire. The inner catheter and outer catheter 68 may be translated together until the detent is positioned at the desired location (such as over the recessed portion 24). The inner catheter may then be withdrawn allowing the detent to compress against the guide wire.

Figure 9:
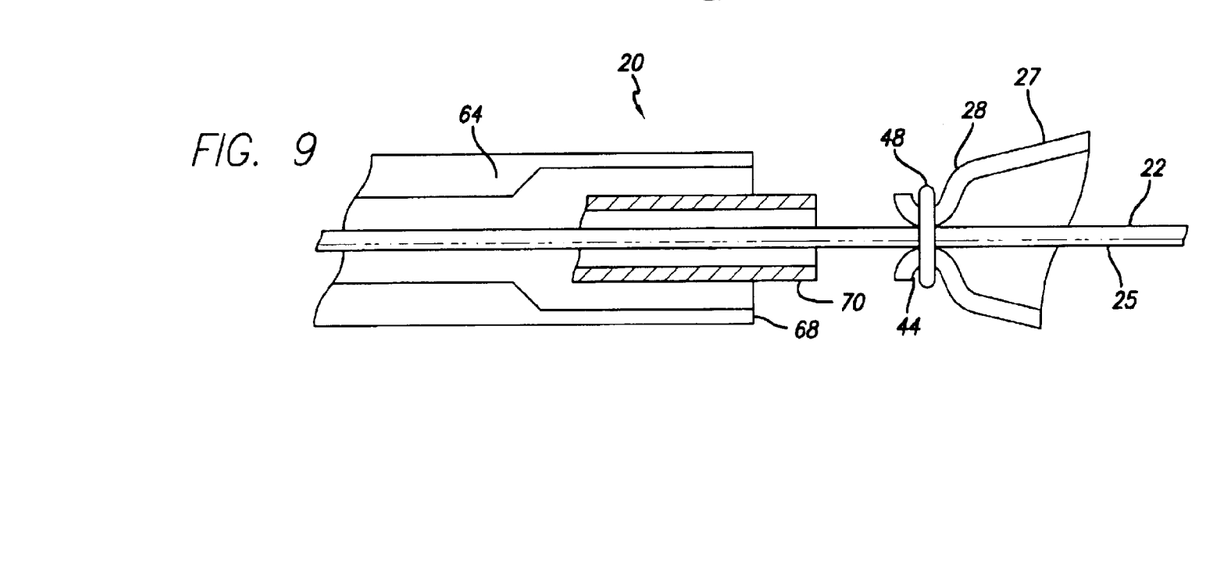
FIG. 9 is a side view of a delivery system for an intraluminal treatment device.

As depicted in FIG. 9 it may be possible to employ the detents 28 onto a guide wire 22 not having a recessed portion. In this configuration, the detents may have enough compressive force to clamp onto the guide wire without a recessed portion and still prevent translation of the treatment device 27. This configuration might still allow relative rotation of the guide wire without disturbing the placement of the treatment device. The use of the inner catheter 70 to prevent contact between the detents and the guide wire during delivery is particularly useful in this configuration. This configuration is applicable both to detents 28 having U-shaped ends 44 and to grommets 50 with inwardly bent ends 52. In the latter configuration, the inwardly bent ends may be sharpened just enough to cause minimal distortion in the guide wire 22. This would allow the treatment device 27 to rotate but not move along the wire.

Figure 10:
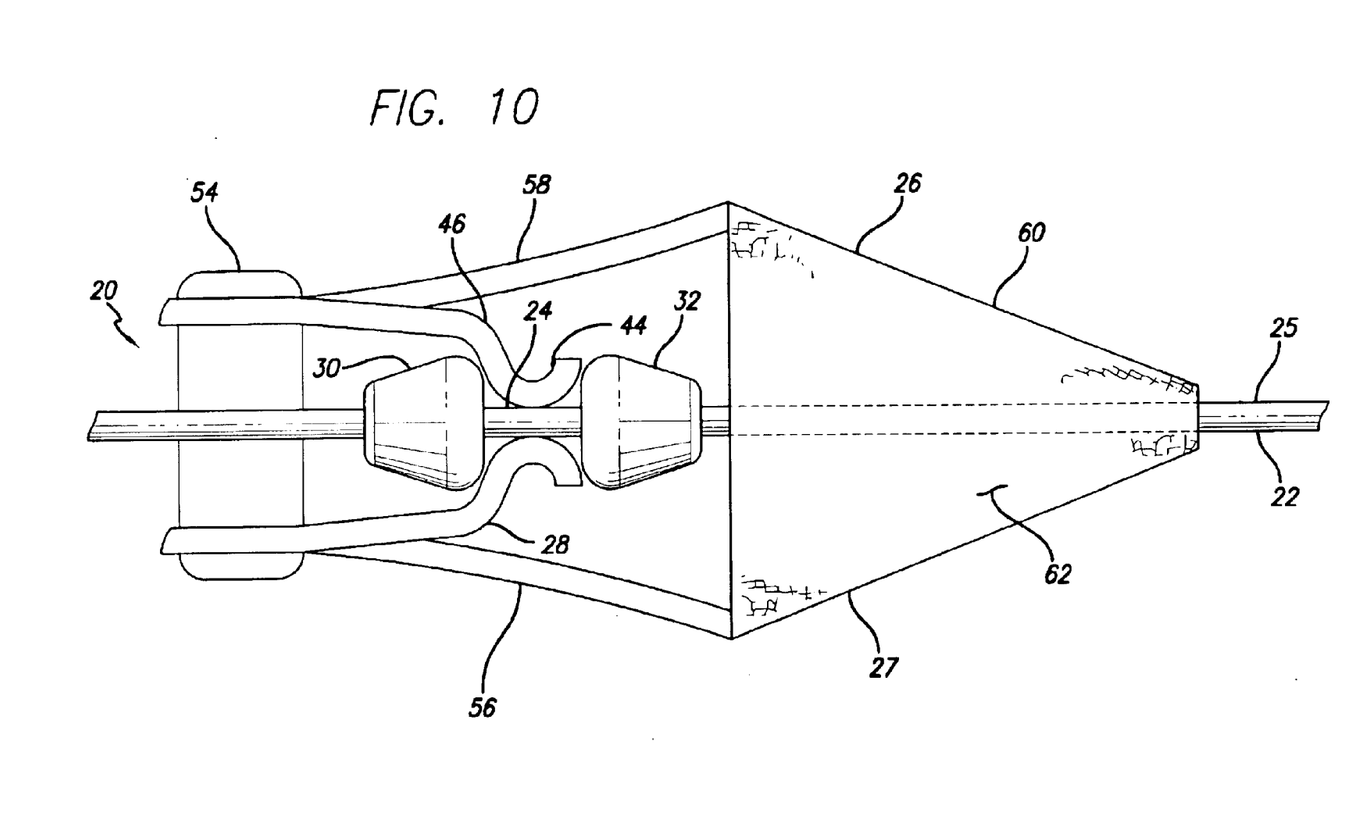
FIG. 10 is a side view of an intraluminal treatment device.

The particular orientation of the components of this invention may be varied from what is described herein. As an example, FIG. 10 depicts a configuration of the detents 28, wherein the body extension 46 extends proximally from the U-shaped end 44. This configuration is also possible with detents having a grommet 50 and an inwardly bent end 52. This configuration of the invention has the advantage that the combination of the treatment device 27 and the guide wire attaching mechanisms are in a more compact arrangement which may facilitate delivery.

Those of skill in the art will appreciate that there may be many variations to the embodiments described herein. Thus, these embodiments are intended as examples and do not limit the scope of the invention. It is intended that the following claims cover the described embodiments and the variations that fall within their scope.

What is claimed is:

1. A system for intraluminal delivery of an embolic cage, comprising:
    a guide wire having a distal end and a proximal end;
    a slot on the guide wire located near the distal end;
    an embolic cage slidably disposed over the guide wire;
    at least one detent on the embolic cage configured to securedly engage the slot.

2. The system of claim 1, wherein at least one detent engages the slot with compressive forces.

3. The system of claim 2, wherein the detent is formed from a grommet having an inwardly bent end.

4. The system of claim 2, wherein the detent is formed from a spring-loaded appendage.

5. The system of claim 1, wherein the slot is formed by a localized grind in the guide wire.

6. The system of claim 1, wherein the slot is formed between two bushings adhered to the guide wire.

7. The system of claim 1, wherein the slot is formed within a single bushing adhered to the guide wire.

8. The system of claim 1, wherein the secure engagement between the detent and slot allows for rotation but not translation of the embolic cage relative to the guide wire.

9. A system for attaching an intraluminal device to a guide wire, comprising:
    a guide wire having a distal tip;
    a first bushing on the guide wire located near the distal tip;
    a second bushing on the guide wire located proximal to the first bushing;
    an intraluminal device slidably disposed on the guide wire; and
    at least two spring-loaded appendages attached to the intraluminal device in compressive contact with the guide wire,
    whereby the appendages prevent sliding of the intraluminal device while the appendages contact the guide wire between the first bushing and the second bushing.

10. The system of claim 9, further comprising:
    a compressive strap around the at least two spring-loaded appendages.

11. The system of claim 9, wherein the second bushing on the guide wire has a proximal taper.

12. The system of claim 9, further comprising:
    a sleeve connecting the at least two appendages to the intraluminal treatment device.

13. The system of claim 9, wherein the appendages include a U-shaped end in contact with the guide wire.

14. The system of claim 9, wherein the intraluminal device and spring-loaded appendages are collapsed for delivery and expanded for treatment.

15. A system for securing an intraluminal treatment device to a guide wire, comprising:
    a guide wire having a recessed portion;
    an expandable intraluminal treatment device having a detent in compressive contact around the guide wire;
    a delivery catheter disposed over the intraluminal treatment device and the guide wire; and
    the delivery catheter is configured to slide the treatment device over the guide wire until the detent is positioned over the recessed portion.

16. The system of claim 15, wherein the recessed portion of the guide wire is formed between two bushings adhered to the guide wire.

17. The system of claim 15, wherein the inner diameter of the delivery catheter is sized to prevent the delivery catheter from advancing beyond the bushings.

18. The system of claim 15, further comprising a bushing on the guide wire located at the distal end of the recessed portion.

* * * * *